(12) United States Patent
Jaenicke et al.

(10) Patent No.: US 6,458,384 B2
(45) Date of Patent: Oct. 1, 2002

(54) PHARMACEUTICAL WITH PREDETERMINED ACTIVITY PROFILE

(75) Inventors: Christof Jaenicke; Jörg Grünwald, both of Berlin (DE); Benedikt Hänggi, Arlesheim (CH)

(73) Assignee: Impetus AG (CH)

( * ) Notice: Subject to any disclaimer, the term of this patent is extended or adjusted under 35 U.S.C. 154(b) by 0 days.

(21) Appl. No.: 09/790,582

(22) Filed: Feb. 23, 2001

(30) Foreign Application Priority Data

Feb. 23, 2000 (CH) ............................................. 347/00

(51) Int. Cl.$^7$ ................................................. A61K 9/22
(52) U.S. Cl. ...................... 424/468; 424/725; 424/730; 424/733; 424/736; 424/746; 424/757; 424/768
(58) Field of Search ................................ 424/725, 730, 424/733, 736, 746, 757, 468

(56) References Cited

U.S. PATENT DOCUMENTS

| | | |
|---|---|---|
| 3,287,220 A | 11/1966 | Martin |
| 5,213,808 A | 5/1993 | Bar-Shalom et al. |
| 5,229,131 A | 7/1993 | Amidon et al. |
| 5,407,686 A | 4/1995 | Patel et al. |
| 5,738,874 A | 4/1998 | Conte et al. |
| 5,788,987 A | 8/1998 | Busetti et al. |
| 5,840,329 A | 11/1998 | Bai |
| 5,879,710 A | 3/1999 | Bromet |
| 5,929,058 A | 7/1999 | Deisher |
| 5,935,975 A | 8/1999 | Rose et al. |
| 6,015,789 A | 1/2000 | Suzuki et al. |
| 6,034,105 A * | 3/2000 | Mendel |

FOREIGN PATENT DOCUMENTS

| | | |
|---|---|---|
| DE | 4325465 | 2/1995 |
| FR | 2340087 | 9/1977 |
| FR | 2584604 | 1/1987 |
| GB | 791644 | 3/1958 |
| WO | WO99/32119 | 7/1999 |

OTHER PUBLICATIONS http://www.nutritionfocus.com/nutrition_supplementation/herbs/index.htm, 1999.*
"Dictionnaire Vidal", p. 806, col. 3, 1997 (with translation).
"Pharmaceutical Dosage Forms", Hans Hess (ed.), ISBN–No. 3–456–81334–1, copy of pp. 7, 11–25 and 73–77.
Gunny, Tabert (ed.), "Pulsatile Drug Delivery: Current Applications and Future Trends", Chapter III and Chapter VII, 1993.

* cited by examiner

Primary Examiner—Leon B. Lankford, Jr.
Assistant Examiner—Ruth A. Davis
(74) Attorney, Agent, or Firm—Burns, Doane, Swecker & Mathis, L.L.P.

(57) ABSTRACT

A first pharmacologically active substance contained in a pharmaceutical, which acts on a specific biological function, is released according to a predetermined release profile (D.1), FIG. 1, and generates a first activity profile (I.1) that has flank phases with increasing and decreasing activity intensity. For changing such flank phases, an additional pharmacologically active substance is used which acts on the same biological function and which is released according to a release profile (D.2) such that its activity profile (I.2) overlays the first activity profile (I.1) within the flank phase to be changed. For shortening an end flank phase, an additional substance is used whose activity is counter to the activity of the first substance and cancels, reduces, or overpowers this activity in its declining phase. Accordingly, with the aforementioned pharmaceutical, undesirable aftereffects of a pharmacologically active substance, for example, can be prevented. In one embodiment, a sedative is contained as a first pharmacologically active substance, which is released immediately, and a stimulant, which is released with delay and thus counteracts uncomfortable aftereffects of the sedative in its end phase, is contained as an additional pharmacologically active substance.

17 Claims, 5 Drawing Sheets

PHARMACEUTICAL WITH PREDETERMINED ACTIVITY PROFILE

SUMMARY OF THE INVENTION

The invention relates to a pharmaceutical in which a first pharmacologically active substance, or a pharmaceutically acceptable salt thereof, which acts on a specific biological function, is integrated such therein that it is released according to a predetermined first release profile (D.1), which generates a first activity profile (I.1) with at least one flank of increasing and at least one flank of decreasing activity intensity, especially a set forth below, processes for the manufacture thereof and to methods of treatment comprising administering such a pharmaceutical.

BACKGROUND OF THE INVENTION

Pharmaceuticals contain at least one pharmacologically active substance which, after administration of the pharmaceutical to a human or an animal, is to act via biological-chemical pathways in regard to at least one biological function of the human or animal, wherein the activity may be of a therapeutic or prophylactic nature or desired for other reasons. In many cases, the requirements placed on the pharmaceutical not only relate to a specific type of action but also a specific temporal course of the activity intensity, i.e., a specific activity profile.

The activity profile of an administered pharmacologically active substance is not directly measurable in many cases. However, based on medical experience and optionally with the aid of the temporal course of the corresponding blood level, the activity profile can be deduced for large groups of pharmacologically active substances and for different administration methods with sufficient reliability.

The type of action as well as the activity profile of a pharmaceutical, respectively, of a pharmacologically active substance contained in the pharmaceutical depend on pharmacodynamic parameters which determine the effect of the active substance on the organism (in particular, dosage and responsiveness) and on the pharmacokinetic parameters which determine the effect of the organism on the active substance (in particular, resorption, distribution, and storage in the organism as well as elimination by excretion or metabolism). It is attempted in many different ways to produce pharmaceuticals by which not only a pharmacologically active substance is administered to the organism but by which also additionally at least some of the above-mentioned parameters can be affected such that an activity profile that is as optimal as possible for the application is achieved with a dosage that is as minimal as possible.

For generating an activity profile as advantageous as possible, the pharmacologically active substance is administered according to a selected administration profile (administration dosage as a function of time), in a selected form (for example, lipid-soluble or water-soluble), and in a selected way (orally, intravenously, intramuscularly, etc.), the pharmaceutical is designed such that the substance according to a selected release profile (the amount of the active substance released in the organism as a function of time), and/or additional active substances are administered as "regulating substances" which regulating substances act on the organism in the sense of an advantageous control of the pharmacokinetics of the pharmacologically active substance.

Particularly for pharmaceuticals which are orally administered, a plurality of methods are known in order to generate for the pharmacologically active substances contained in the pharmaceutical freely selectable release profiles within wide limits. Such release profiles comprise, for example, a delayed release (for example, according to U.S. Pat. No. 5,788,987), a release as uniformly as possible over a time period as long as possible or a pulsatile release over an extended period of time (for example, according to U.S. Pat. No. 5,229,131). Moreover, administration forms are known in which two or more release types are combined to a release profile such that, for example, of a pharmacologically active substance a first portion is immediately released (burst) and the residual amount is distributed over a longer period of time (for example, according to U.S. Pat. Nos. 5,879,710, 5,738,874, or 5,407,686) or that, after a uniform release over a certain period of time, a release burst takes place (according to U.S. Pat. No. 5,213,808). It has also been proposed to administer the pharmacologically active substance in the form of a plurality of particles, wherein particles, which are designed for different release times, can be combined to a mixture with a substantially freely selectable release profile (for example, according to U.S. Pat. No. 5,840,329).

It is also known to employ administration forms in which different release types are combined with one another for the combined administration of more than one pharmacologically active substance wherein, for example, a first one of the substances is designed to provide a desired pharmacological activity and wherein a further one of the substances is administered for regulating the pharmacokinetics of the first substance. The administration of a substance (for example, benserazide or carbidopa), which is administered in combination with L-dopa against Parkinson's disease and which is released before L-dopa, as described, for example, in U.S. Pat. No. 5,738,874, is to be understood in this way. The regulating substance delays the metabolism of L-dopa to dopamine and ensures that a quantity as large as possible of the administered amount reaches in the form of unchanged L-dopa the blood-brain interface which it can pass only in this unchanged form. In a similar way, substances for inhibiting or ameliorating the undesirable side effects of a first active substance are released as, for example, the release of a substance, described in the same publication, for inhibiting irritation of the mucous membranes of the gastrointestinal tract before the release of a pharmacologically active substance which irritates these mucous membranes as an undesirable side effect.

With the above addressed pharmaceuticals it is thus attempted, in particular, via the release profile and via the pharmacokinetics, to adapt the activity profile of a pharmacologically active substance to specific requirements, wherein, however, a plurality of parameters which determine such an activity profile, in particular, such parameters which are coupled with one another, may remain unaffected.

DE 43 25 465 describes a pharmaceutical allowing release of an opioid antagonist before an opioid agonist. The former shall overcome the paralytic effects of the opioid on peristaltic motion of the gut leading to constipation, while the therapeutic effect of the opioid agonist is not negatively affected. GB 791 644 describes the timely staggered use of glutarimide in a pharmaceutical in combination with barbiturates in order to overcome toxic effects of barbiturate overdosing. In both cases, the drugs to be released at different time points are combined such that the negative and undesirable effects of an active compound (paralysis of peristaltic motion, toxicity) are diminished while the desired activity remains intact.. On the other hand, U.S. Pat. No. 3,287,220 describes the increase in activity of a drug cocktail against asthma by a protease that is encapsulated in the core of a solid pharmaceutical also comprising the members of the drug cocktail. FR 25 84 604 describes the use of combinations of two pharmaceuticals, especially analgetics, A and B where one of these components is integrated such into a pharmaceutical that it is released fast, the other in a retarded way, so that the (analgetic) activity starts fast due to the fast release of the first component and lasts longer due to slower release of the second. Finally, FR 23 46 087 describes the combination of a soporific drug and a blood pressure stabilizing/circulation enhancing drug that is released some time after the soporific drug in order to maintain sleep in elder people by avoiding their awakening due to a critical lowering of blood pressure that occurs late in the night. In all these cases, the combinations are intended to support or enhance the effect of a drug on the same biologic phenomenon (antiasthmatic effect, pain reduction or sleep, respectively) by another compound in the same direction.

None of these references that always deal with synergistic combinations or combinations where one of the combination partners just has the task to compensate for an undesired effect of the other partners suggests or in any way supports the idea of the present invention:

GENERAL DESCRIPTION OF THE INVENTION

The invention has the object to provide a pharmaceutical with which it is possible to design, as desired, flank phases of the activity profile (phases in which the activity intensity increases or decreases significantly) of a pharmacologically active substance, in particular, end flank phases with decreasing activity or, in a different aspect of the invention, initial flank phases with increasing activity intensity, without, however, affecting other phases of the activity profile and without reducing the design freedom for such other phases.

Figure 1:
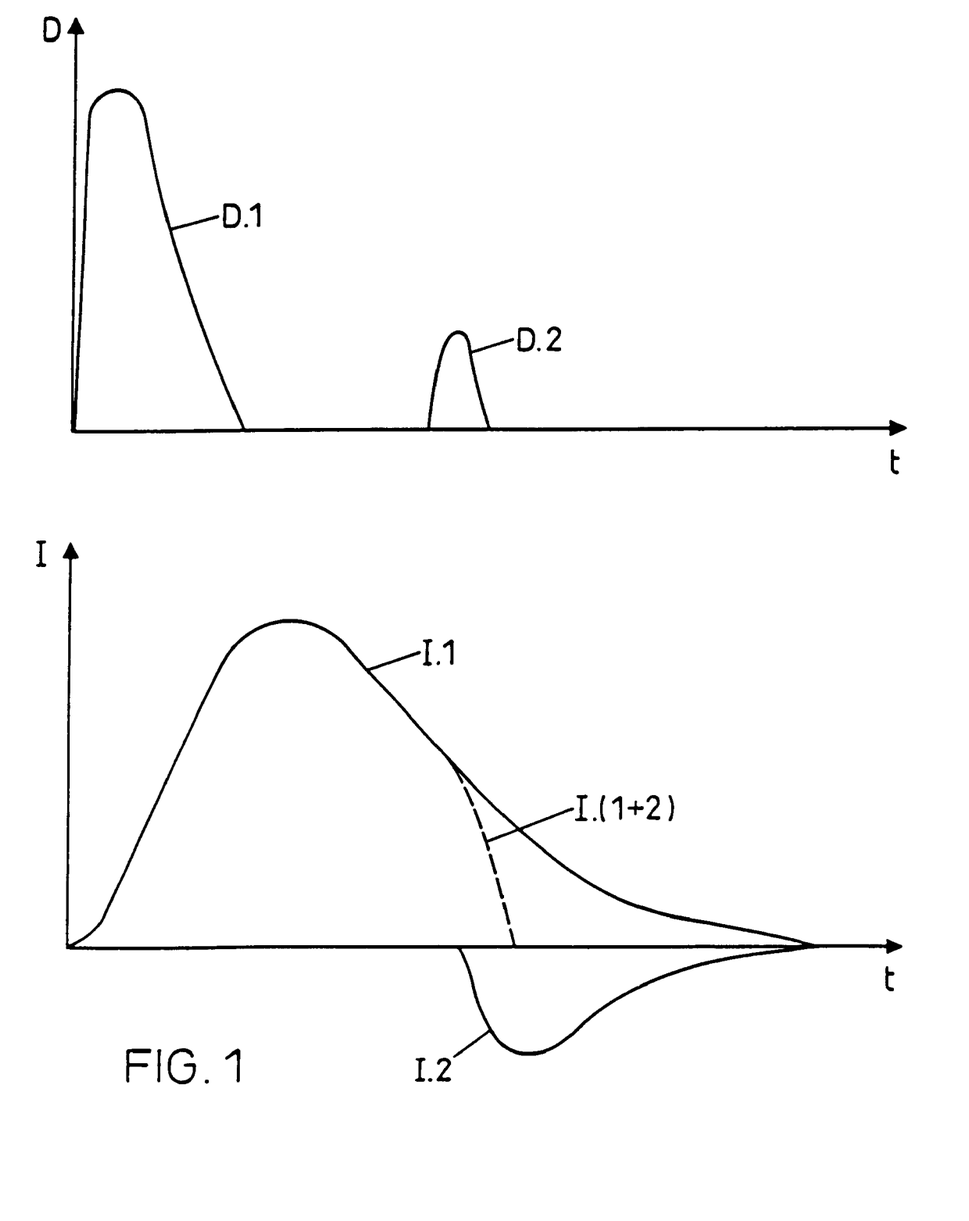
FIGS. 1 and 2 release and activity profiles of two embodiments of the pharmaceutical according to the invention with shortened end flank phase for the activity of a first pharmacologically active substance.
Figure 2:
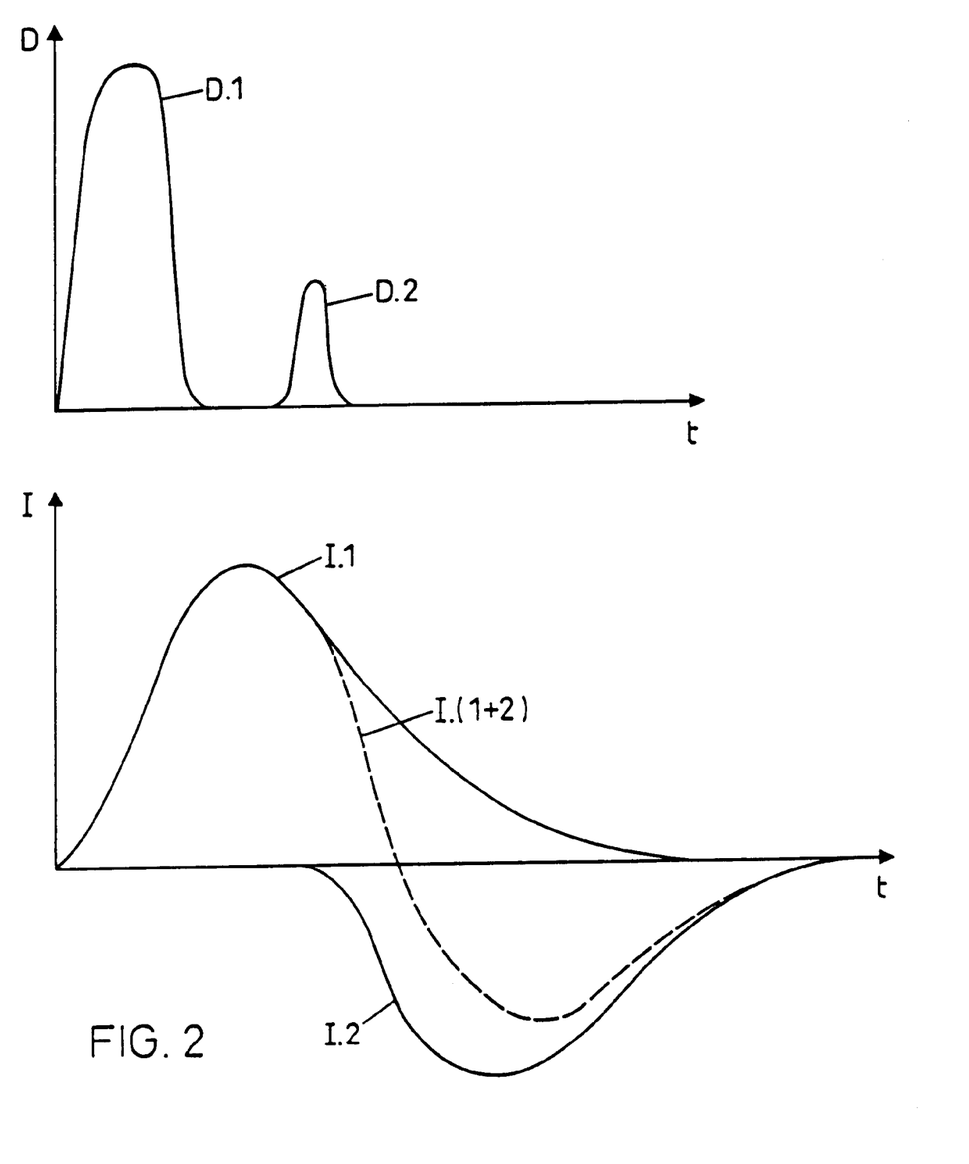
Figure 3:
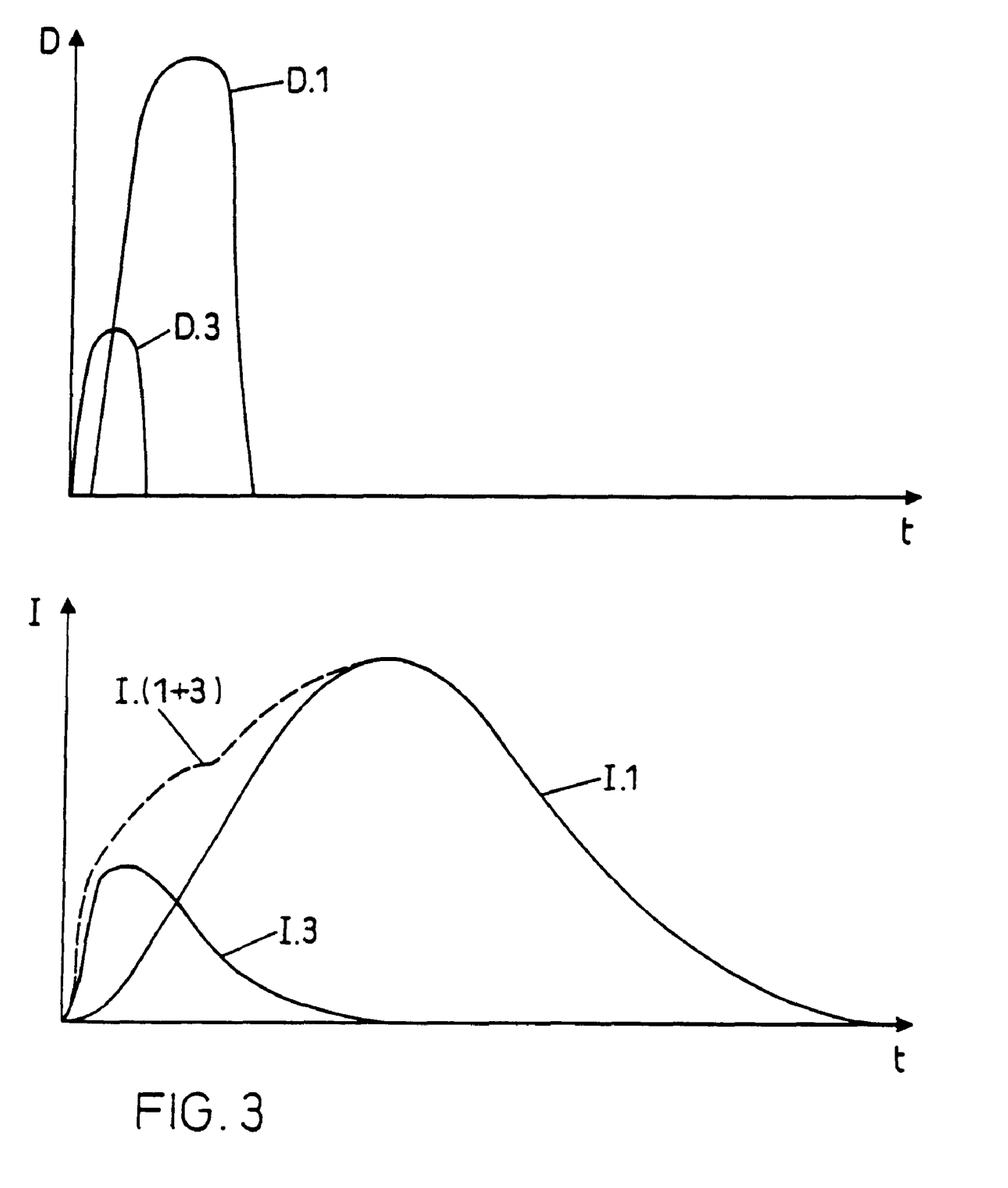
FIG. 3 release and activity profiles of an embodiment of the pharmaceutical according to the invention with shortened initial flank phase for the activity of a first pharmacologically active substance.

The invention relates to a pharmaceutical comprising (i) a first pharmacologically active substance, which acts on a specific biological function, which substance is integrated such into the pharmaceutical that it is released according to a predetermined first release profile (D.1), which generates a first activity profile (I.1) with at least one flank of increasing and at least one flank of decreasing activity intensity, and (ii) for changing at least one flank phase of the first activity profile (I.1) an additional pharmacologically active substance having activity on the same biological function in a modifying way and which is integrated such that it is released according to a second release profile (D.2, D.3) which generates a second activity profile (I.2, I.3), wherein the second activity profile (I.2, I.3) overlaps the flank phase of the first activity profile (I.1) to be changed; with the proviso that where the term substance is used this refers to the respective compound and/or a pharmaceutically acceptable salt thereof (reference signs refer to FIGS. 1–3).

The resulting modification of the effect of said first pharmacologically active substance by said additional pharmacologically active substance is an approach that is totally different from the prior art combinations.

The preferred pharmaceutical according to the invention is thus based on the principle of affecting in a desired way flank phases of the activity profile of a first pharmacologically active substance, whose activity relates to a specific biological function, by over-laying it with at least one other activity profile of an additional pharmacologically active substance acting on the same biological function in a modifying way, preferably in a way antagonizing the effect on the same biological function of said first pharmacologically active substance.

In other terms, for shortening the phase of a decreasing end flank of the activity profile of a first pharmacologically active substance, a second substance is therefore used which has an antagonizing action on the same biological function as the action of the first substance and which is released such that its activity profile overlaps the activity profile of the first substance in the end flank phase. This provides an activity combination in which the two oppositely directed activities overcome one another at least partially.

Applications for this administration form of the pharmaceutical according to the invention can be found, in particular, where temporally sharply limited activities of relatively high intensity are required or desired, i.e., where an underlying "after-effect" of a pharmacologically active substance is to be suppressed. This is, for example, the case for soporific agents whose activity, in particular, in high dosages with an uncomfortably long end phase is not sufficient for sleeping and is not beneficial for the waking state. This end phase of the activity of an active substance is significantly shortened according to the invention by the counteracting substance, in the case of a soporific agent by a stimulating agent or dopant which is released for its activity in the end flank phase.

Conversely, according to a different aspect of the invention, for shortening an ascending initial flank of the activity profile of a first pharmacologically active substance whose activity relates to a specific biological function, a second pharmacologically active substance of same activity is used such that the second activity profile overlaps the flank phase of the first activity profile and accelerates the activity increase in this phase.

For shortening the initial flank phase of an active substance having a strong activity, being side effect-reduced or otherwise advantageous but acting for some reason only with undesirably great delay, it is therefore possible to employ in the initial flank phase a small dosage of a substance of same activity but being less advantageous for some reason, wherein, especially, undesirable side effects of the second substance have no consequence as a result of the temporally very limited and very small dosage.

The combined pharmacologically active substances in the pharmaceutical according to the invention could also be taken or administered separately. However, the combination in a single pharmaceutical has the advantage, on the one hand, of improved patient compliance in the case of a planned pharmacological treatment and, on the other hand, an a priori avoidance of uncomfortable side effects which therefore do not occur at all and which must not be fought deliberately after their occurrence. Accordingly, the acceptance of a pharmacologically active substance can be considerably improved.

DESCRIPTION OF THE FIGURES

With the aid of the following Figures the principle of the pharmaceutical according to the invention and exemplary embodiments of this pharmaceutical will be explained in detail. It is shown in.

FIGS. 1 to 3 show a release profile and an activity profile of the pharmaceutical according to the invention, wherein in the release profile the released dosage D as a function of time t and in the activity profile the activity intensity I as a function of time are plotted. The pharmaceutical according to the invention contains in all three cases two pharmacologically active substances with a release profile D(t) and an activity profile I(t), respectively, wherein the activity profiles relative to the release profiles show a temporal delay determined substantially by the resorption and distribution within the organism and an aftereffect determined essentially by the metabolism or excretion and following the release with delay.

FIG. 1 illustrates the shortening of the end flank phase of the activity profile I.1 of a first pharmacologically active substance 1 with a release profile D.1 by an activity profile I.2 of an additional counteracting substance 2 (counteraction represented as an activity intensity with reverse sign) overlaying the end flank phase. The combined activity I.(1+2) shows relative to I.1 a drastically shortened end flank phase. For realizing the activity profile I.(1+2) illustrated in FIG. 1 with shortened end flank phase the counteracting substance is bound in the pharmaceutical such that it is released with delay relative to the first substance 1. As illustrated, the first substance 1, in this connection, can be released substantially in an undelayed burst; however, it can also be released with delay and/or over a longer time period. In any case, the release D.2 of the counteracting substance is to be determined such that its activity overlays the end flank phase of the activity profile of the first substance 1.

An example for the embodiment of the pharmaceutical according to the invention illustrated in FIG. 1 contains a sedative or soporific agent, for example, comprised of valerian or hop, as well as at least one stimulating agent or dopant, for example, caffeine, theophylline or theobromine. The release of the sedative is initial so that the effect occurs immediately. The release of the stimulating agent or dopant is delayed such that the decreasing but still present activity of the sedative or soporific agent after 12 h, especially after 1, 2, 4, 6, 8 or 10 hours, as selected, is overlayed by the activity of the stimulating agent or dopant and is thus substantially cancelled.

In this connection, the release profile of the stimulating agent or dopant can be such that it neither lasts longer than nor surpasses the effect of the sedative, as is illustrated in FIG. 1, or it can do both so that the effect of the sedative or soporific agent in the end stage is not only cancelled but immediately replaced by the stimulating activity of the stimulating agent or dopant. Release and activity profiles for such an embodiment of the pharmaceutical according to the invention are illustrated in FIG. 2, wherein the same functions are identified with the same reference numerals.

One example of an embodiment of the pharmaceutical according to the invention with an activity as illustrated in FIG. 2 contains a stimulant, which is released and develops its activity first, and a sedative or soporific agent, with which the end flank of the stimulant is shortened and whose activity replaces the activity of the stimulant immediately.

FIG. 3 illustrates the shortening of the initial flank phase of the activity profile I.1 of the first pharmacologically active substance 1 by the identically acting additional substance 3 which overlays this initial flank phase with its activity profile I.3.

DETAILED DESCRIPTION OF THE INVENTION AND ITS PREFERRED ASPECTS

The general terms used herebefore and hereinafter preferably have the meanings indicated below, unless indicated otherwise, whereby the more specific meanings may be used independently of one another in preferred embodiments of the present invention instead of the general definitions, embodiments with these more specific meanings then describing especially preferred embodiments of the invention.

"Comprising" stands for "containing at least" or "including", meaning that also other components may be present; preferably up to 30 further components, more preferably up to 16, Where the term "flank" or "flank phase" is used, this refers to either those phases where the respective active substance is set free at a decreasing or increasing rate, or preferably where the blood level of the respective substance is increasing or decreasing, or most preferably where the activity on a biological function is increasing or decreasing.

The term "release profile" refers to the pattern of release of the respective pharmacologically active substance over time, that is, the amount released over time. This may be measured either in vivo, e.g. indirectly by measuring the blood concentration, or preferably ex vivo, e.g. by the USP paddle method that allows for determination of the dissolution rate of the substance. For example, a USP paddle apparatus operating at 37° C. and 50 rpm ist used and the preparations are tested in (e.g. 900 ml) artificial intestinal fluid, e.g. phosphate buffer pH 6.8; artificial gastric juice, e.g. 0.1 N HCl; or water. Samples are withdrawn for determination of the amount of substance released in intervals of e.g. 30 or 60 min an analysed, e.g. spectrophotometrically, for example at 272 nm for caffeine, and/or using HPLC methods. A preferred method is described in the examples that may be used in analogy for other pharmaceuticals according to the invention. Preferred methods for analyzing blood or plasma levels of compounds are also described in the examples—analogous methods can be used for different active substances and are known int the art or easily derivable from the art.

The term "activity profile" refers to the pattern of activity of the respective pharmacologically active substance over time, which can be expressed either in terms of the blood concentration over time or the biological activity over time (e.g. for sleep induction and/or maintenance determination of paramaters indicating sleepiness; for stimulating substances determination of parameters indicating stimulation; in both cases, parameters may inter alia be obtained by standard methods, such as methods for the determination of central nervous system activity, e.g.EEG, EMG or EOG or tomographic measurements, or psychological test methods, e.g. for determining concentration and/or performance, or the like.

The term "biological function" is synonymous to "biological status" or "physiological status"; preferred is a biological function that has two or more states both of which are desirable at different time points, for example the status of activity of the (especially central) nervous system, e.g. an active status, characterized e.g. by alertness or excitability, or a muted status, e.g. characterized by sedation, drowsyness or sleep. Other examples of biological functions include e.g. blood pressure (high or low), digestion (low or high gut motility), and the like.

By the term "with activity on the same biological function in a modifying way" there is especially meant that a first pharmacologically active substance has a different effect on a biological function than an additional active substance that also forms part of a phamaceutical according to the invention. Preferably, the additional active substance may partially or fully compensate (e.g. remove a muted central nervous state induced by the first pharmacologically active substance) or preferably even antagonize (counteract) an effect of the first pharmacologically active substance (e.g. lead to stimulation of the central nervous system after it has been muted by the first pharmacologically active substance). This modifying effect may result from activity on the same or different targets, e.g. receptors, cell systems or the like. The term "antagonize" is thus preferably meant to comprise both functional antagonism (based on an effect on the same cell system of the first and the additional pharmacologically active substance, respectively) and physiological antagonism (based on an effect on different cell systems of said substances), resulting in an opposite action on the biological function to be modified. It does not, however, refer to a mere compensation of a toxic effect or an undesired effect of one of the substances by the other.

That a substance is "integrated such . . . that it is released" according to a certain release profile or such as to show a certain activity profile preferably means that the pharmaceutical according to the invention makes use of the known methods, e.g. those mentioned above or below, to formulate drugs so that they are set free at certain time points, e.g. when compared with the USP paddle method or in vivo methods, especially as described above or below.

The first and additional pharmacologically active substances or agents (e.g. active ingredients, e.g. sedatives, soporific agents, sleeping aids for falling asleep, sleeping agents for sleeping through, stimulants, dopants, antidepressants, dextroamphetamines etc.) comprised by the pharmaceuticals according to the invention may be present as such or, if they carry salt-forming groups, such as basic groups or acidic groups in the form of pharmaceutically acceptable salts. Where these substances or agents are mentioned, this is intended to comprise the free compound or the pharmacologically active salts thereof.

Pharmaceutically acceptable salts are formed, for example, from substances or agents having an acid group, for example a carboxy group, a sulfo group, or a phosphoryl group substituted by one or two hydroxy groups, and are, for example, salts thereof with suitable bases, such as non-toxic metal salts derived from metals of groups Ia, Ib, IIa and IIb of the Periodic Table of the Elements, especially suitable alkali metal salts, for example lithium, sodium or potassium salts, or alkaline earth metal salts, for example magnesium or calcium salts, also zinc salts or ammonium salts, as well as salts formed with organic amines, especially mono-, di- or tri-lower alkylamines, or with quaternary ammonium compounds, such as tetrabutylammonium salts. Substances and agents having a basic group, for example an amino group, can form acid addition salts, for example with inorganic acids, e.g. hydrohalic acids, such as hydrochloric acid, sulfuric acid or phosphoric acid, or with organic carboxylic, sulfonic, sulfo or phospho acids or N-substituted sulfamic acids, for example acetic acid, propionic acid, amino acids, especially glutamic acid and aspartic acid, or with methanesulfonic acid, ethanesulfonic acid. Substances or agents with both acid and basic groups can also form internal salts.

For the preparation of the pharmaceutical according to the invention, manufacturing methods which are known in the art can be used, in particular, manufacturing methods for pharmaceuticals in which different release profiles are realized, for example:

swelling/erosion-controlled (or induced) initial release;
breakage/fracture-controlled (or induced) initial release;
ion exchange-controlled (or induced) initial release.

Any galenical composition, as well as methods for ist manufacture, can be used for developing the pharmaceuticals comprising delayed release compositions according to the invention.

Some publications which relate to this subject matter have been mentioned supra, while further possible forms are described e.g. in Pulsatile Drug Delivery: Current Applications and Future Trends, T. Gurny (ed.), Stuttgart, Wissenschaftliche Verlagsgesellschaft 1993, especially chapters III and VII as well as the references quoted there-in. All these publications and references are also incorporated by reference herein. Numerous appropriate compositions and procedures are known to the skilled person. As a further example, the TheriForm™ method (Therics, Inc.), a manufacturing process working in a manner very similar to an "ink jet" printer to create a precise three-dimensional product composed of a series of two-dimensional layers, and the resulting products are applicable.

Suitable are, for example, solid, oral administration forms (for example, tablets, capsules or sachets). For their manufacture, a mixture of a powder and granules with a coating is produced wherein the substance to be released first is in the powder, the substance to be released with delay is in the granules, and the mixture is then pressed to tablets or is filled into hard gelatin capsules or sachets. The magnitude of the delay for such administration forms depends substantially on the properties of the coating of the granules.

Among the ingredients useful for such preparations the following are of special interest:

| Excipient type | Excipients |
| --- | --- |
| Acidifying agents | Citric acid; Fumaric acid; Hydrochloric acid; Malic acid; Phosphoric acid; Propionic acid; Sulfuric acid; Tartaric acid |
| Alkalising agents | Ammonia solution; Ammonium carbonate; Potassium hydroxide; Sodium bicarbonate; Sodium borate; Sodium carbonate; Sodium hydroxide; di-sodium tartrate, succinic acid-disodium hexahydrate |
| Antifoaming agents | Dimethicone; Simethicone |
| Binder | Acacia; Alginic acid; Carboxymethylcellulose, sodium; Cellulose, microcrystalline; Dextrin; Ethylcellulose; Gelatine, Glucose; Guar gum; Hydroxypropyl methylcellulose; Methylcellulose; Polyethylene oxide; Povidone; Starch, pregelatinised; Syrup |
| Coating agents | Ammonio methacrylate copolymers, Carboxymethylcellulose, sodium; Cellulose acetate; Cellulose acetate phthalate; Cetyl alcohol; Ethylcellulose; Gelatine; Hard fat; Hydroxypropylcellulose; Hydroxypropyl methylcellulose; Hydroxypropyl methylcellulose phthalate; Methacrylic acid copolymer; Polyethylene glycol; Polyvinylacetate phthalate; Shellac; Sucrose; Wax; Zein; ethyl cellulose; Ammonium methacrylate copolymer |
| Coloring agents | Iron oxide, Titanium dioxide |
| Complexing agents | Edetate disodium; Edetate acid; |
| Diluents | Calcium Carbonate; Calcium phosphate, dibasic; Calcium phosphate, tribasic; Calcium sulfate; Cellulose, microcrystalline; Cellulose, powdered; Dextrates; Dextrin; Fructose; Kaolin; Lactose; Mannitol; Sorbitol; Starch; Starch, pregelatinsed; Sucrose |
| Disintegrants | Alginic acid; Cellulose, microcrystalline; Crosscarmellose sodium, Crospovidone; Polacrilin potassium; Sodium starch glycolate; Starch; Starch, pregelatinised; Carboxymethycellulose sodium |
| Emulsifying agents | Lecithin; Poloxamer; Polysorbates; Sodium lauryl sulfate; Stearic acid |
| Flavours | Ethyl vanillin; Vanillin; others |

-continued

| Excipient type | Excipients |
|---|---|
| Glidants | Calcium silicate; Magnesium silikate; Silicon dioxide, colloidal; Talc |
| Lipophilic matrix Formers | Castor oil, hydrogenated; Cetyl alcohol; Hard fat; Wax |
| Lubricants | Calcium stearate; Glyceryl behenate; Magnesium stearate; Mineral oil; Polyethylene glycol; Sodium stearyl fumarate; Stearic acid; Talc; Vegetable oil; Zinc stearate |
| Plasticizers | Castor oil; Diacetylated monoglycerides; Dibutyl sebacate; Diethyl phthalate; Glycerin; Mono- and Di-acetylated monoglycerides; Polyethylene glycol; Propylene glycol; Triacetin; Triethylcitrate |
| Sequestring agents | Beta cyclodextrin |
| Solvents | Acetone; Alcohols; Methylene chloride; Water |
| Sweetening agents | Aspartame; Dextrates; Dextrose; Fructose; Mannitol; Saccharin; Saccharin calcium; Saccharin sodium; Sorbitol; Sucrose; Sugar; Syrup |
| Vehicles | Syrup; oils; sugar spheres |
| Viscosity increasing agents | Alginic acid; Bentonite; Carbomer; Carboxy-methylcellulose calcium; Carborymethylcellulose sodium; Carragenan; Cellulose, microcrystalline; Carboxymethylcellulose disodium; Dextrin; Gelatine; Guar gum; Hydroxyethyl cellulose; Hydroxyproyl cellulose; Hydroxypropyl methylcellulose; Magnesium aluminium silikate; Methylcellulose; Pectin; Polyethylene oxide; Silicon dioxide; Silicon dioxide, colloidal; Sodium alginate; Tragacanth; Xanthan gum |
| Antiadhering agents | Precipitated silicon dioxide |

Especially preferred ingredients, also used in the Examples,

| Excipient/Active ingredient and pharmacop. status | Supplier |
|---|---|
| Aerosil 200, Colloidal silicon dioxide, USP/NF | Degussa |
| Aqualon EC N-10 Pharm., Ethylcellulose, USP/NF | Hercules |
| Avicel PH 101, 102, 105, Microcrystalline cellulose, USP/NF | FMC |
| Caffeine anhydrous, BP 93 | Selectchemie |
| Cellulose acetate CA 320-S, Cellulose acetate, USP/NF | Eastman |
| Cellulose acetate CA 398-10 NF, Cellulose acetate, USP/NF | Eastman |
| Dibutyl sebacate, USP/NF | Morfelx |
| Di-sodium tartrate, dihydrate | Fluka |
| Ethanol | Fluka |
| Eudragit RL 30 D, Ammonio methacrylate copolymer, Type A, USP/NF | Rohm |
| Eudragit RS 30 D, Ammonio methacrylate copolymer, Type B, USP/NF | Rohm |
| Isopropanol | Fluka |
| Kollidon CL, Crospovidone, USP/NF | BASF |
| Kollidon K 30, Povidone, USP/NF | BASF |
| Magnesium stearate, USP/NF | Faci |
| Maize starch, Eur. Ph. | Roquette |
| Methanol | Fluka |
| Methocel K4M Premium EP, Hydroxypropyl methylcellulose, USP/NF | Colorcon |
| Methocel E4M Premium EP, Hydroxypropyl methylcellulose, USP/NF | Colorcon |
| Methocel E15LV Premium EP, Hydroxypropyl methylcelloluse, USP/NF | Colorcon |
| Methocel A4M Premium EP, Methylcellulose, USP/NF | Colorcon |
| Methylene chloride | Fluka |
| Pharmatose DCL 11, Lactose monhydrate, USP/NF | DMV International |
| Pharmatose 200 M, Lactose monohydrate, USP/NF | DMV International |
| Sodium acetate, anhydrous | Sigma |
| Succinic acid disodium salt, hexahydrate | Fluka |
| Syloid 244 FP, precipitated silicon dioxide, USP/NF | Grace |
| Talc, USP/NF | Selectchemie |
| Triethylcitrate, USP/NF | Morflex |

PREFERRED EMBODIMENTS OF THE INVENTION

In addition to oral administration forms, implants, suppositories, skin patches, mucous membrane patches, adhesive bandages, or in a less preferred aspect of the invention injection solutions (e.g. mixtures of depot form and free form of first and additional substance, respectively) or corresponding infusion solutions are suitable as administration forms for the pharmaceuticals according to the invention, especially as mentioned above and below, wherein in this connection the required release profiles can be realized without problems by a person skilled in the art.

The dose of each of the first and the additional pharmacologically active substance or substances (active ingredients) depends on the age, weight and individual condition, on individual pharmacokinetic conditions, and on the mode of administration. The preferred dose to be administered to warm-blooded animals for each of the active ingredients, especially to a human of approximately 70 kg body weight, is in the range of approximately 0.1 mg to approximately 5 g, preferably from approximately 1 mg to approximately 3 g, most preferably from approximately 1 mg to approximately 500 mg, For example, melatonin is present in an amount of 0.1 to 25, preferably 0.1 to 10 mg per unit dosage form (e.g. tablet or capsule), and caffeine in an amount of 20 to 1000, preferably 50 to 500 mg per unit dosage form. Children receive less than adults, for example, half of the adult dose. "Approximately" preferably stands for a deviation of ±10%, more preferably of ±2% from the given numeric value; most preferably, the given number is meant. The pharmaceutical compositions preferably comprise from 1% to 95%, especially from 2% to 60%, of all active ingredients taken together.

The invention preferably relates to a pharmaceutical as described above, wherein the additional pharmacologically active substance antagonizes the activity of the first pharmacologically active substance on the specific biological function and wherein the additional substance is integrated in a way to be released such that its activity shortens a phase with decreasing activity intensity of the first activity profile (FIG. 1, FIG. 2, (I.1)).

More preferred is a pharmaceutical, especially according to the previous paragraph, wherein the phase with decreasing activity intensity of the first activity profile (FIG. 1, FIG. 2, (I.1)) is an end phase and the additional pharmacological active substance is integrated in a way to be released such that its activity lasts until beyond the activity of the first substance and replaces it.

The embodiments mentioned above in the description of the invention of pharmaceuticals according to the invention comprise, especially as the first pharmacologically active substance, or alternatively as the additional pharmacologically active substance) a sedative or soporific agent and a stimulating agent or dopant. These terms are to be understood very broadly and are meant to encompass, on the one hand, tranquilizers, sleeping aids, sleeping agents and the like., and, on the other hand, stimulating agents, dopants, waking agents, antidepressants and the like.

The aforementioned agents for tranquilizing or for sleeping are synthetic active substances such as, for example, melatonin (N-acetyl-5-methoxytryptamine; especially preferred)), a melatonin agonist, Gaba (gamma-aminobutyric acid), antihistamines (for example, benocten), benzodiazepines (for example, midazolam, diazepam), diazepines, phenobarbiturates, diphenhydramines or methiazoles. Or they are active substances which are contained in plant extracts: *Valeriana officinalis, Lavandula angustifolia, Humulus lupulus, passiflora incarnate, Ocimum basilicum, Nardostachysjatamamsi, Hypericum perforatum, Corydalis cava, Daliva miltiorrhiza, Cyperipedium pubescens, Cymbopogon flexuosus, Melissa officinalis, Monarda didymia, Citrus aurantii, Psicidia piscioula.*

Preferred is also a pharmaceutical as described hereinbefore or hereinafter wherein either the first an/or the additional pharmacologically active substance (especially the latter) is a stimulant or dopant or an agent supporting waking.

The known stimulants, dopants or agents which support waking, are synthetic substances as, preferably methyl xanthines (for example, caffeine, theophylline, theobromine), amphetamines (such as dextroamphetamine or methamphetamine), pemolines, methylphenidates (for example, methyl phenidate hydrochloride) or modafinil; or antidepressants, especially selected from the group consisting of imipramine, desipramine, clomipramine, protriptyline, fluoxetine, paroxetine, sertraline, citalopram, fluvoxamine, paroxetine, fluoxetine, sertraline, amitriptyline, desipramine, nortriptyline, mirtazepine, venlafaxine, pheneizine, tranylcypromine, nefazodone, trazodone and buprion; or dextroamphetamine. Especially preferred are caffeine (most preferred), theophylline or theobromine, or a pharmaceutically acceptable salt thereof.

Or they are substances which are contained in plant extracts: caffeine-containing, theophylline-containing, theobromine-containing plants, *Paullinia cupana, Crataegus laevigata, Syzyium aromaticum, Ilex paraguariensis, Piper methysticum, Cola acuminita, Folium cocae, Semen myristicae, Ephedra sinica, Tunera diffusa.*

Especially preferred is a pharmaceutical as described hereinbefore, wherein the first pharmacologically active substance is a sedative or a soporific agent, the additional pharmacologically active substance is a stimulant or dopant, and the first pharmacologically active substance is integrated in a way to be released immediately and the second pharmacologically active substance is integrated in a way to be released with delay.

More preferred is a pharmaceutical according to the last paragraph, wherein the additional pharmacologically active substance is integrated in a way to be released with a delay, as desired, of up to 12 hours, preferably 1 to 10 hours, more preferably 4 to 9 hours, and most preferably 6 to 8 hours.

Still more preferred is a pharmaceutical as described hereinbefore, wherein the first pharmacologically active substance is a combination of a sleeping aid for falling asleep and a sleeping agent for sleeping through, the additional pharmacologically active substance is a stimulating agent or dopant, and the sleeping aid is integrated in a way to be released immediately, the sleeping agent is integrated in a way to be released with delay, and the additional pharmacologically active substance is integrated in a way to be released with delay relative to the sleeping agent.

Even more preferred is a pharmaceutical according to the last paragraph, wherein the release of the sleeping agent is delayed, as selected, by 1 to 6 hours and the additional pharmacologically active substance is released with a delay of 2 to 6 hours relative to the sleeping agent.

Also more preferred is a pharmaceutical as described hereinbefore, wherein the first pharmacologically active substance is a stimulating agent or dopant, the additional pharmacologically active substance is a sedative or a soporific agent, and the first pharmacologically active substance is integrated in a way to be released immediately and the additional pharmacologically active substance is integrated in a way to be released with delay.

More preferred is a pharmaceutical according to the last paragraph, wherein the additional pharmacologically active substance is integrated in a way to be released with a delay of 2 to 6 hours; or wherein the stimulating agent or the dopant is integrated in a way to be released immediately and at least once with delay and the sedative or soporific agent is integrated in a way that, with respect to the last release of the stimulating agent or dopant, it is released with delay; especially wherein the stimulating agent or the soporific agent is integrated in a way to be released immediately and with a delay of, as desired, 1, 2, 3, 4, 5 and/or 6 hours and the sedative or soporific agent is integrated in a way that, relative to the last release of the stimulating agent or dopant, it is released with a delay of two to six hours.

For generating the first and/or the second activity profile, the pharmaceutical according to the invention may contain not only one (first or additional) pharmacologically active substance, respectively, but also correspondingly active substance combinations, i.e., it can contain more than two active substances (a plurality of pharmacologically active substances, preferably 2 to 5). In this connection, the individual components of the active substance combinations are released according to the same or (preferably) different release profiles.

An example for an embodiment of the pharmaceutical according to the invention with more than two pharmacologically active substances is an agent against the inability to fall asleep and to sleep through which agent contains a sleeping aid (immediate release) for falling asleep, a sleeping agent (release delayed by 1, 2, 3, 4, 5 and/or 6 hours) to sleep through, and a stimulant (release, for example, 2–6 hours after the last release of the sleeping agent), and in which essentially the end flank phase of the activity of the sleeping agent is shortened by the stimulant and optionally replaced by it. The activity profiles illustrated in FIGS. 1 to 3 of the first and/or of the second pharmacologically active substance in a pharmaceutical according to the invention can also be generated by several releases of such substances.

An example of several releases or a release over a longer period of time of the first pharmacologically active substance is an agent for shift workers, night duty or against jet lag which contains a dopant (release immediately and after 1, 2, 3, 4 and/or 6 hours) and a sleeping aid (release 2 to 6 hours after last release of the stimulant) wherein the activity of the sleeping aid shortens the end flank phase of the activity of the dopant and replaces it immediately.

The invention relates also to a method of treatment comprising administering a pharmaceutical according to the invention to a mammal, especially a human, requiring such treatment, e.g. in order to treat sleep disorders, or especially adverse phenomena associated with jet lag, shift work or night duty; where preferably a pharmaceutical according to the invention comprising the active ingredients, especially those mentioned as being preferred, in the doses given above is administered. In the case of the combination of a fast release soporific agent, especially melatonin, as sleeping aid and a late release stimulant, especially caffeine, the pharmaceutical is preferably administered prior to sleep, e.g. up to 120 min prior to sleep, preferably 10 to 60 min prior to sleep, preferably the melatonin being used in a dose from 1 to 10 mg, especially 1 to 6 mg, more preferably 2 to 3 mg for an adult, the stimulant, especially caffeine, in the doses indicated above or below. If melatonin is used for treatment of jet-lag in combination with a late release stimulant, the dose of melatonin is preferably in the range from 0.1 to 2 mg, more 0.1 and 1 mg, most preferably 0.3 to 0.6 mg, escpecially 0.5 mg, that of the stimulant as indicated above or below. For the time of administration of melatonin comprising pharmaceuticals according to the invention it has to be taken into account how much the "biological clock" has to be put forward or back: For west-east flights (e.g. Los Angeles to New York) and a time difference of 3 to 8 h, the administration is in the evening of the "eastern" time and at least 1 to 2 h before going to sleep. Thus the biological clock us out forward (advance of the body clock). For west-east flights and a time difference of more than 8 h, e.g. 9 to 11 h, the administration takes place in the morning of the "eastern" time (delay of the body clock). For east-west flights, the administration preferably takes place in the morning according to "western" time after awaking (delay of the body clock).

EXAMPLES

In the following examples, which are intended to illustrate the invention without affecting the scope thereof, formulations for the pharmaceutical according to the invention are described, in particular, for an embodiment which contains a sedative (valerian or melatonin) and a stimulant (caffeine), wherein the sedative is released immediately and the stimulant is released with a delay of an order of magnitude of five hours. Such a pharmaceutical provides for deep sleep and a refreshed awakening shortly after the release of the stimulant without the aftereffects of the sedative. For a longer or shorter effect of the sedative, the formulations must be adjusted accordingly.

Where not indicated otherwise, percentages or other relative indications of amounts are given on a weight by weight (w:w) basis. The dissolution rate determination using the USP paddle apparatus has already been described above. The attrition rate of tablet cores for subsequent film-coating is preferably determined under standard conditions in a friabilator. The rate of attrition, i.e. the friability, is calculated. Tablets exhibiting a friability of 1% or less are preferably developed for film-coating. The crushing strength of tablets is determined in a tablet hardness tester (N=10).

Among the equipment used is:

| Piece of equipment | Manufacturer |
| --- | --- |
| Diffusion blend T2 C | Bachofen |
| Drying cabinet | Salvis |
| Fluid bed dryer/coater/granulator Strea I | Aeromatic |
| Laboratory kneader | Kenwood |
| Single screw extruder ET 35 T | Gabler |
| Single station compression machine Comprex | Jörgensen |
| Single station compression machine EKO DMS | Korsch |
| Sphaeromat SPH-250 | Wyss + Probst |
| Tablet disintegration tester DT 3 | Sotax |
| Tablet dissolution tester AT 6 | Sotax |
| Tablet friability tester | Kühner |
| Tablet hardness tester 6 D | Schleuniger |
| Uvikon 710 spectrophotometer | Kontron |

Example 1

Pharmaceutical According to the Invention with Valerian and Caffeine in a Sachet form for Oral Administration Valerian extract, microcrystalline cellulose, lactose, cornstarch, and silicon dioxide are mixed in a free fall mixer for 10 minutes. Subsequently, magnesium stearate is added which has been de-agglomerated by passing it through a mesh of 0.9 mm, followed by mixing again for five minutes. The powder mixture is then compacted with a roll compactor to scabs of approximately 1.5 mm thickness. The obtained scabs are comminuted to granules on a granulating machine by a mesh having a mesh width of 1.25 mm. The obtained granules are coated in a fluidized bed with an inflow air temperature of 40–45° C. and an exhaust air temperature of 30–35° C. with a dispersion of methyl hydroxy propyl cellulose, polyethylene glycol 8000 (according to Arzneibuch: Macrogol 8000) and silicon dioxide in dichloromethane/methanol, 9:1 (G/G), and subsequently dried.

Caffeine, sodium chloride, and microcrystalline cellulose are mixed in a quick mixer for three minutes, sufficient water is added, followed by kneading. The moistened material is then extruded in an extruder through a perforated plate with a mesh width of 0.8 mm to form strands. The extruded mass is rounded on a rounding device to pellets with an average grain size of 0.9–1.0 mm. The thus obtained pellets are then coated in a fluidized bed with an inflow air temperature of 45–50° C. and an exhaust air temperature of 35–40° C. with a film comprised of cellulose acetate, Macrogol 8000, and methyl hydroxy propyl cellulose. Cellulose acetate, Macrogol 8000 and methyl hydroxy propyl cellulose have been dissolved beforehand in dichloromethane/methyl, 9:1 (GIG).

The coated granules and the coated pellets are combined, talcum, passed through a mesh of 0.9 mm, and silicon dioxide are added, followed by mixing for 10 minutes. 528 mg are filled into a sachet, respectively.

| Example 1: Sachet formulation | | | |
|---|---|---|---|
| | (mg) | (%) | (%) |
| Valerian Granules | | | |
| Valerian extract | 125.0 | 55.6 | 21.5 |
| Microcrystalline cellulose | 48.0 | 21.3 | 8.2 |
| Magnesium stearate | 2.0 | 0.9 | 0.3 |
| Lactose | 25.0 | 11.1 | 4.3 |
| Silicon dioxide | 5.0 | 2.2 | 0.9 |
| Cornstarch | 20.0 | 8.9 | 3.4 |
| Subtotal | 225.0 | 100.0 | |
| Film-Coating for Valerian Granules | | | |
| Methyl hydroxy propyl cellulose | 12.0 | 60.0 | 2.1 |
| Macrogol 8000 | 6.0 | 30.0 | 1.0 |
| Silicon dioxide | 2.0 | 10.0 | 0.3 |
| Dichloromethane/methanol, 9:1 (w/w), q.s. | * | * | * |
| Subtotal | 20.0 | 100.0 | |
| Caffeine Pellet | | | |
| Caffeine | 200.0 | 66.7 | 34.4 |
| Sodium chloride | 50.0 | 16.7 | 8.6 |
| Microcrystalline cellulose | 50.0 | 16.7 | 8.6 |
| Water, q.s. | * | * | * |
| Subtotal | 300.0 | 100.0 | |
| Film-Coating for Caffeine Pellet | | | |
| Cellulose acetate | 25.0 | 83.3 | 4.3 |
| Methyl hydroxy propyl cellulose | 2.0 | 6.7 | 0.3 |
| Macrogol 8000 | 3.0 | 10.0 | 0.5 |
| Dichloromethane/methanol, 9:1 (w:w), q.s. | * | * | * |
| Subtotal | 30.0 | 100.0 | |
| Outer Phase | | | |
| Silicon dioxide | 1.0 | 14.3 | 0.2 |
| Talcum | 6.0 | 85.7 | 1.0 |
| Subtotal | 7.0 | 100.0 | |
| Total | 582.0 | | 100.0 | q.s. = quantum satis, * = is removed again during the manufacturing process
Release According to USP
Media: 0.1 N HCl 0–120 min., phosphate buffer pH = 6.8 > 120 min, 37° C.
Release apparatus: USP Paddle
Speed: 50 rpm

| | Time (min) | | | | | | | | | |
|---|---|---|---|---|---|---|---|---|---|---|
| Accumulated rel | 15 (%) | 30 (%) | 60 (%) | 120 (%) | 180 (%) | 240 (%) | 300 (%) | 330 (%) | 360 (%) | 420 (%) |
| Valerian | 57.0 | 98.9 | 99.9 | 100.0 | | | | | | |
| Caffeine | 0.0 | 0.0 | 0.0 | 0.0 | 0.0 | 0.0 | 0.0 | 87.0 | 99.0 | 99.5 |

Figure 4:
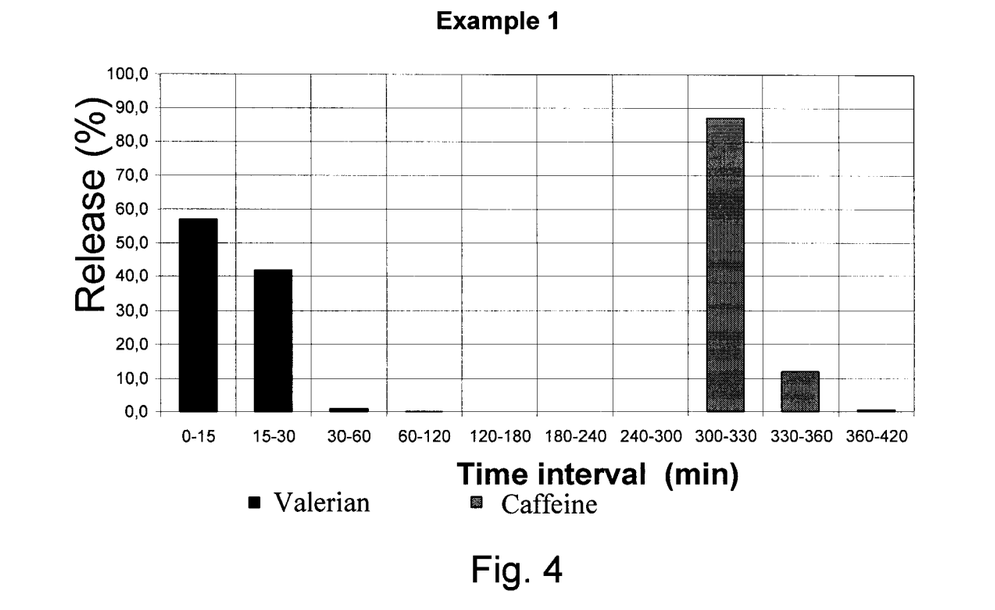
FIGS. 4, 5, and 6 release profiles of the embodiments of the pharmaceutical according to the invention according to the examples 1, 2, and 3.

FIG. 4 shows the release profiles for valerian and caffeine from a sachet according to example 1.

Example 2
Pharmaceutical According to the Invention with Valerian and Caffeine in Tablet form for Oral Administration Methyl hydroxy propyl cellulose is dissolved in sufficient water. Caffeine, mannite, and silicon dioxide are added with stirring and dispersed with a homogenizer. The nonpareils are sprayed in a fluidized bed with the above described dispersion at an inflow air temperature of 45–50° C. and an exhaust air temperature of 35–40° C. and subsequently dried.

The caffeine-containing pellets are coated in a fluidized bed with a solution of cellulose acetate, methyl hydroxy propyl cellulose, and Macrogol 8000 in dichloromethane/methanol, 9:1 (G:G) at an inflow air temperature of 45–50° C. and an exhaust air temperature of 35–40° C. and subsequently dried in the fluidized bed.

The valerian extract is mixed with lactose, microcrystalline cellulose, cornstarch, and silicon dioxide in a free fall mixer for 10 minutes. Subsequently, magnesium stearate is added which has been passed through a mesh of 0.9 mm, followed by mixing for five minutes.

The caffeine pellets coated with cellulose acetate are mixed with the valerian tablet mixture in a free fall mixer for 10 minutes and are then pressed in a tablet machine to tablets of a weight of 934 mg.

Example 2: Tablet Formulation

|  | (mg) | (%) | (%) |
|---|---|---|---|
| Caffeine Pellets |  |  |  |
| Nonpareils, 300–400 µm | 200.0 | 40.0 | 21.4 |
| Caffeine | 200.0 | 40.0 | 21.4 |
| Methyl hydroxy propyl cellulose | 20.0 | 4.0 | 2.1 |
| Mannite | 70.0 | 14.0 | 7.5 |
| Silicon dioxide | 10.0 | 2.0 | 1.1 |
| Water, q.s. | * | * | * |
| Subtotal | 500.0 | 100.0 |  |
| Film-Coating for Caffeine Pellets |  |  |  |
| Cellulose acetate | 30.0 | 88.2 | 3.2 |
| Methyl hydroxy propyl cellulose | 2.0 | 5.9 | 0.2 |
| Macrogol 8000 | 2.0 | 5.9 | 0.2 |
| Dichloromethane/methanol, 9:1 (w:w) | * | * | * |
| Subtotal | 34.0 | 100.0 |  |
| Valerian Tablet Mixture |  |  |  |
| Valerian extract | 125.0 | 31.3 | 13.4 |
| Lactose | 125.0 | 31.3 | 13.4 |
| Microcrystalline cellulose | 104.0 | 26.0 | 11.1 |
| Cornstarch | 40.0 | 10.0 | 4.3 |
| Magnesium stearate | 4.0 | 1.0 | 0.4 |
| Silicon dioxide | 2.0 | 0.5 | 0.2 |
| Subtotal | 400.0 | 100.0 |  |
| Total | 934.0 |  | 100.0 | q.s. = quantum satis, * = is removed again during the manufacturing process
Release According to USP
Media: 0.1 N HCl 0–120 min., phosphate buffer pH = 6.8 > 120 min, 37° C.
Release apparatus: USP Paddle
Speed: 50 rpm

|  | Time (min) | | | | | | | | | |
|---|---|---|---|---|---|---|---|---|---|---|
| Accumulated rel | 15 (%) | 30 (%) | 60 (%) | 120 (%) | 180 (%) | 240 (%) | 300 (%) | 330 (%) | 360 (%) | 420 (%) |
| Valerian | 43.0 | 78.4 | 96.8 | 100.0 |  |  |  |  |  |  |
| Caffeine | 0.0 | 0.0 | 0.0 | 0.0 | 0.0 | 0.0 | 15.0 | 89.3 | 99.5 | 99.7 |

Figure 5:
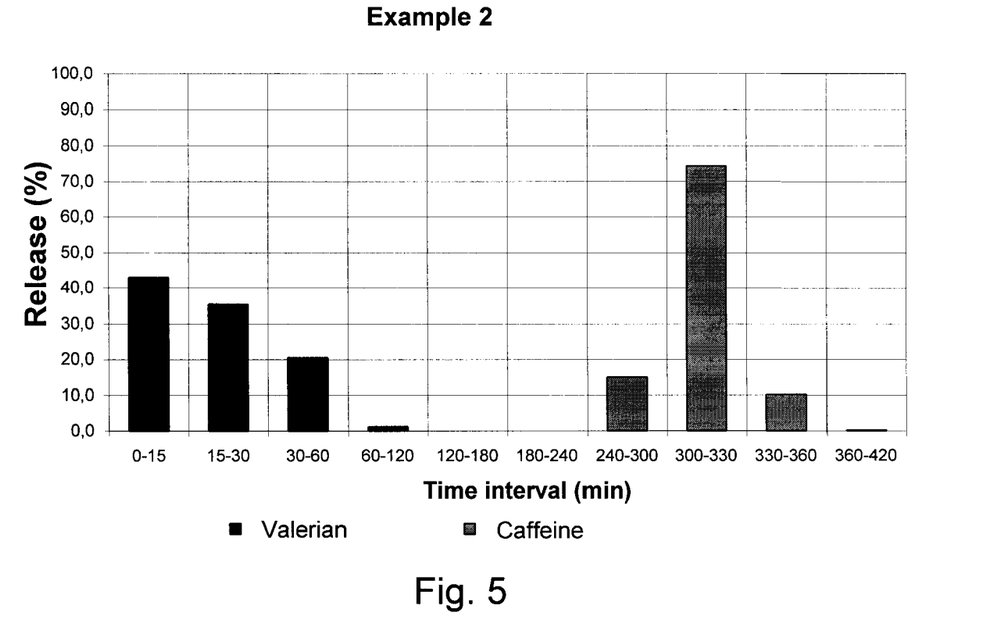

FIG. 5 shows the release profiles for valerian and caffeine from the tablet according to example 2.

Example 3

Pharmaceutical According to the Invention with Valerian and Caffeine in Tablet form for Oral Administration Caffeine, microcrystalline cellulose, lactose, cross-linked polyvinyl pyrrolidone and silicon dioxide are mixed in a free fall mixer for 10 minutes. Magnesium stearate, passed through a mesh of 0.9 mm, is added and mixed together with the powder mixture containing the active substances for an additional 5 minutes. The homogeneous powder mixture is then compacted by means of roll compaction to scabs of approximately 1.5 mm thickness. The scabs are then broken by a granulating machine with a mesh width of 1.25 mm. The granules are classified. The granule fraction between 0.7 and 1.1 mm is used for further processing.

The caffeine granules of the grain fraction 0.7–1.1 mm is coated with a protective lacquer of methyl hydroxy propyl cellulose, Macrogol 8000 and silicon dioxide in a fluidized bed with an inflow air temperature of 40–45° C. and an exhaust air temperature of 30–35° C. Subsequently, the granules coated with the protective lacquer are lacquered with a solution of ethyl cellulose and dibutyl sebacate in isopropanol in a fluidized bed at an inflow air temperature of 30° C. and an exhaust air temperature of 28° C. The lacquered granules are then dried in the fluidized bed apparatus at an inflow air temperature of 35° C.

The valerian extract is mixed with lactose, microcrystalline cellulose, cornstarch, and silicon dioxide in a free fall mixer for 10 minutes. Subsequently, magnesium stearate which has been de-agglomerated by passing it through a mesh of 0.9 mm is added, followed by mixing for another five minutes.

The caffeine granules coated with methyl hydroxy propyl cellulose and ethyl cellulose are mixed with the valerian tablet mixture in a free fall mixer for five minutes and subsequently pressed in a tablet press to tablets with a weight of 1,055 mg.

Example 3: Tablet Formulation

|  | (mg) | (%) | (%) |
|---|---|---|---|
| Caffeine Granules | | | |
| Caffeine | 200.0 | 41.1 | 19.0 |
| Microcrystalline cellulose | 80.0 | 16.4 | 7.6 |
| Lactose | 120.0 | 24.6 | 11.4 |
| Polyvinyl pyrrolidone, cross-linked | 80.0 | 16.4 | 7.6 |
| Magnesium stearate | 5.0 | 1.0 | 0.5 |
| Silicon dioxide | 2.0 | 0.4 | 0.2 |
| Subtotal | 487.0 | 100.0 | |
| Film Coating for Caffeine Granules | | | |
| Protective Lacquer | | | |
| Methyl hydroxy propyl cellulose | 50.0 | 86.2 | 4.7 |
| Macrogod 8000 | 5.0 | 8.6 | 0.5 |
| Silicon dioxide | 3.0 | 5.2 | 0.3 |
| Water, q.s. | * | * | * |
| Subtotal | 58.0 | 100.0 | |
| Control Lacquer | | | |
| Ethyl cellulose | 100.0 | 90.9 | 9.5 |
| Dibutyl sebacate | 10.0 | 9.1 | 0.9 |
| Isopropanol, q.s. | * | * | * |
| Subtotal | 110.0 | 100.0 | |
| Valerian Tablet Mixture | | | |
| Valerian extract | 125.0 | 31.3 | 11.8 |
| Lactose | 125.0 | 31.3 | 11.8 |
| Microcrystalline cellulose | 104.0 | 26.0 | 9.9 |
| Cornstarch | 40.0 | 10.0 | 3.8 |
| Magnesium stearate | 4.0 | 1.0 | 0.4 |
| Silicon dioxide | 2.0 | 0.5 | 0.2 |
| Subtotal | 400.0 | 100.0 | |
| Total | 1,055.0 | | 100.0 | q.s. = quantum satis, * = is removed during the manufacturing process
Release According to USP
Media: 0.1 N HCl 0–120 min., phosphate buffer pH = 6.8 > 120 min, 37° C.
Release apparatus: USP Paddle
Speed: 50 rpm

| | Time (min) | | | | | | | | | |
|---|---|---|---|---|---|---|---|---|---|---|
| Accumulated release | 15 (%) | 30 (%) | 60 (%) | 120 (%) | 180 (%) | 240 (%) | 300 (%) | 330 (%) | 360 (%) | 420 (%) |
| Valerian | 59.6 | 95.6 | 99.4 | 99.9 | | | | | | |
| Caffeine | 0.0 | 0.0 | 0.0 | 0.0 | 0.0 | 0.0 | 5.3 | 85.6 | 99.0 | 99.2 |

Figure 6:
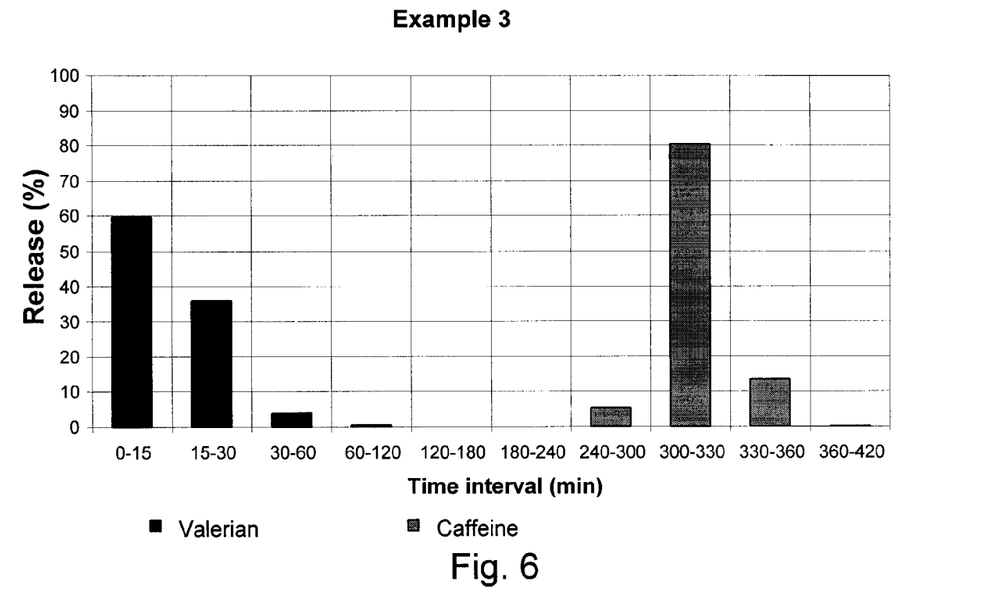

FIG. 6 shows the release profiles for valerian and caffeine from a tablet according to example 3.

Example 4
Melatonin/Caffeine Combinations

By using melatonin instead of valerian in Examples 1 to 3, the corresponding combined pharmaceuticals with melatonin in late and caffeine in early release form are prepared and evaluated by the USP paddle test as described.

Example 5
Pressure Controlled Delayed Release Form for Caffeine Useful in Combination with Fast Release Forms of Melatonin Aqualon ethylcellulose is available in four ethoxyl types. The N-type polymer, exhibiting a viscosity of 10 mPas, i.e. Aqualon ethylcellulose N-10, a special NF grade quality, is used as film-coating material to control the release of caffeine. In order to allow for multiple unit formulation with essentially identical surface and particle size characteristics—which are a prerequisite for the development of pressure controlled particle size characteristics—small tablets are produce as core formulations. Kollidon CL (Crospovidone) is used as disintegrant. The Kollidon CL containing tablet cores (composition see table) are coated with an organic solution of ethylcellulose in methanol/methylene chloride. In total, 10 mg ethylcellulose. 100 g of a direct compressible formula containing Caffeine, Kollidon CL, direct compressible Lactose, Avicel PH 102 and Aerosil 200 is pre-blended in a diffusion blender for 5 min and subsequently desagglomerated using a sieve with an aperture width of 0.5 mm. The pre-blend is made up with previously desagglomerated Magnesium stearate and blended for additional 5 minutes to obtain a direct compressible final blend.

| Immediate release tablet | |
|---|---|
| Active ingredient/excipient | Target amount/tablet (mg) |
| Core | |
| Caffeine | 35.0 |
| Lactose DCL 11 | 28.7 |
| Avicel PH 102 | 15.0 |
| Aerosil 200 | 0.3 |
| Kollidon CL | 20.0 |
| Magnesium stearate | 1.0 |
| Total | 100.0 |

The final blend is compressed to 100 mg tablets, diameter 6 mm, comprising 35% caffeine and with a crushing strength of approximately 20 N. The disintegration time of the tablets is <0.5 min.

It is to be noted that the relatively high Lactose content is not mandatory.

The Kollidon CL containing tablet cores (composition see table) are coated with an organic solution of ethylcellulose in isopropanol/dibutyl sebacate—see table:

| Excipient | |
|---|---|
| Aqualon EC N-10 Pharm | 100.0 |
| Dibutyl sebacate | 10.0 |
| Isopropanol | 890.0 |
| Total | 1000.0 |

The ethyl cellulose coating solution is applied onto the caffeine cores in a fluid bed coater operating at an inlet air temperature of 30° C. and an atomizing air pressure of 1.5 bar using a nozzle with an aperture width of 0.8 mm. The flow rate is adjusted to obtain an exhaust air temperature of approximately 28° C. The coating process is interrupted when the applied film-coating solids reach 8%.

When tested in the USP paddle test in phosphate buffer pH 6.8, 5 out of six tested tablets start to release their active ingredient starting 300 to 420 min after the start, then releasing the complete amount of caffeine within 2 hours. One tablet does not rupture at all and thus no caffeine is released from this sample.

Using these tablets, a test preparation comprising the combination of caffeine and melatonin is prepared in the following way: Caffeine tablets, prepared as described above, are filled into gelatine capsules of 1 to 1.5 cm size (6 caffeine tablets per capsule). 0.5 mg of melatonin is added and the capsules (preferably snap-caps) are closed. The capsules are then coated with Eudragit RL 30D (or Eudragit RL 30 S) to be resistant to gastric juice. Due to these properties, the capsules disintegrate fast in the small intestine after passing the stomach, and the melatonin is thus released immediately in the small intestine. The caffeine release, due to the properties of the tablets, starts approximately 420 min later.

Example 6

Patient Trial

The test preparation is a gelatine capsule of size 0 or 00 containing caffeine tablets as described in example 5. In addition, the capsule contains melatonin in the required dose for an adult. For caffeine (treatment of drowsiness or fatigue), a peroral dosage of 200 mg anhydrous caffeine is used. For melatonin (treatment of sleep disorders, environmentally imposed alterations in sleep time schedules) a peroral dose of 6 mg is used. One capsule comprises these amounts of active ingredients.

Four healthy male volunteers of age over 18 until 65, without regular drug treatments and with no drug treatment one week before the trial, are involved. One day before start of the trial and during the trial, the use of coffee, tea and alcohol is strictly forbidden. Only one test group is used, with no control. The health check includes anamnesis, measurement of blood pressure and heart frequency. The study is designed as follows:

In a first part, the test design is explained to the volunteers and they sign a Declaration of informed consent. The health check is made, and basic blood samples are drawn. A basis check of the psychophysiological performance follows.

The second part is the trial itself (first day): Zero samples of blood, start values of the psychophysiological performance are determined. The test preparation is administered (one capsule per participant). Blood sampling 20, 40 and 60 h after administration in order to measure melatonin and 5h 40 min, 6 h, 6 h and 30 min after administration in order to determine caffeine follows.

The samples are identified by volunteer label and sampling time. The blood is collected in plastic tubes prepared with heparin and immediately collected in a refrigerator at +4° C. After at least 15 min, the plasma is separated by centrifugation in cooled tubes. Plasma is carefully transferred into special plastic tubes. The tubes are closed by lid and frozen in the refrigerator up to transport and analysis.

The testing of the psychophysiological performance takes place 90 min after administration (melatonin), 4 h after administration and 6 h after administration (caffeine).

The main target criterion are the observed concentrations of both active ingredients in plasma versus time.

The following methods can be used (also in general, not only in the present clinical setup) for the determination of the caffeine and the melatonin concentration:

The caffeine concentration in plasma is determined using a HPLC method with UV detection, preferably according to O. A. GHOSHEH et al., J. Pharm. Biomed. Anal. 23(2–3), 543–549 (2000) by using a Partisil-10 SCX cation-exchange column (Whatman) and an isocratic mobile phase of sodium phosphate buffer: methanol (92: 8, v/v, 0.1 M, adjusted to pH 4.8 with triethylamine) at a flow rate of 1.5 ml/min, with UV detection at 254 nm.

The melatonin determination in plasma makes use of commercially available RIA-kits or by an HPLC method with high analytical performance, like the method described by J Sastre Torano et al., Biomed. Chromatogr. 14(5), 306–310 (2000), where, after liquid-liquid extraction with dichloromethane under alkaline conditions and evaporation of the solvent, the extract is dissolved in eluent and chromatographed on a base-deactivated octadecyl column, the eluent being prepared from 650 ml potassium dihydrogenphosphate solution (0.07 mol/l water) adjusted to a pH of 3.0 with a 43% phosphoric acid solution, and admixing 350 ml methanol. Detection is via fluorescence at an excitation wavelength of 224 nm and an emission wavelength of 348 nm.

The resulting data serve for the calculation the individual concentration-time curves for melatonin and caffeine. From these curves, the maximum concentrations and the area under the curve are calculated for both active ingredients.

Where applicable, the averages and standard deviations are calculated for all parameters.

The evaluation of individual psychological perormance is based on the hypotheses of Heckhausen, who in principle assumes two basic tendencies of the habitual personality characteristic performance motive:

"Hope of success" (HS)—tendency of confrontation (fight)

"Fear of failure" (FF)—tendency of avoidance.

People who tend to be confident about success are more likely to have a tendency of confrontation in performance situations. For them, copying with tasks and examining the possibilities of the conditions and solutions of the task or demand of the situation at issue is always in the foreground. However, people who are afraid of failure are more likely to show avoidance behavious in performance situations, they assess the possibilities of solving the problem carefully and with restrain, and they are more likely to see the boundary conditions under the aspect of possible unfavorable developments.

The structure and characteristic calue of the test can be characterized as folows: 46 indicators are selected from a preliminary test design with a total of 101 indicators, taking selectivity and difficulty into consideration. They can be distinguished from each other by their good discrimination ability. 16 test indicators relate to hope of success (HS) and 30 to fear of failure. The test subjects sort the indicator sets according to a 7-stage scale. A computer program supples the test set to the test subjects, togerther with the possibilities of the response scale.

HS and FF are evaluated separately. For each category of the scale 1–7, the frequencies (number of mentions/choice in the respective category) are counted and multiplied by the category number. The sum of the products thus obtained is divided by the number of indicators of the respective dimension. This provides the raw values for the tendencies of HS and FF:

$$HS = \frac{\sum_{i=1}^{i=7} (fi \times Xi)}{16}$$

$$FF = \frac{\sum_{i=1}^{i=7} (fi \times Xi)}{30}$$

i=1, . . . 7

Xi=category number fi=frequency of comments per category.

Net hope (NH)=HS-FF indicates which of the tendencies is more pronounced.

What is claimed is:

1. Pharmaceutical comprising (i) a first pharmacologically active substance, which is a sedative, soporific agent, sleeping aid for falling asleep, or sleeping agent for sleeping through, or pharmaceutically acceptable salts thereof intergrated into the pharmaceutical such that it is released according to a predetermined first release profile, and generates a first activity profile with at least one flank of increasing and at least one flank of decreasing activity intensity, and (ii) for changing an end flank phase of the first activity profile, an additional pharmacologically active substance which is a stimulant, dopant or agent supporting walking intergrated such that it is released according to a second release profile which generates a second activity profile, wherein the second activity profile overlaps the end flank phase of the first activity profile to be changed; wherein each pharmacologically active substance is a compound and/or a pharmaceutically acceptable salt thereof.

2. Pharmaceutical according to claim 1, wherein the phase with decreasing activity intensity of the first activity profile of the first pharmacologically active substance is an end phase and the additional pharmacological active substance is integrated in a way to be released such that its activity lasts until beyond the activity of the first substance and replaces it.

3. Pharmaceutical according to claim 1, wherein the first and/or the additional pharmacologically active substance is a substance combination comprised of a plurality of pharmacologically active substances selected from a plurality of sedatives in the case of the first pharmacologically active substance and a plurality of any of stimulants, dopants and agents supporting wakening in the case of the additional pharmacologically active substance.

4. Pharmaceutical according to claim 3, wherein the substances forming the substance combination are released with different release profiles.

5. Pharmaceutical according to claim 1, wherein the first pharmacologically active substance is selected from the group consisting of melatonin (N-acetyl-5-methoxytryptamine), a melatonin agonist, Gaba (gamma-amino-butyric acid), an antihistamine, a benzodiazepine, a diazepine, a phenobarbiturate, diphenhydramine, and a methiazole; or pharmaceutically acceptable salts thereof.

6. Pharmaceutical according to claim 1, wherein the first pharmacologically active substance is melatonin.

7. Pharmaceutical according to claim 1, wherein the first pharmacologically active substance is an active substance of an extract from a plant selected from the group consisting of *Valeriana officinalis, Lavandula angustifolia, Humulus lupulus, Passiflora incarnate, Ocimum basilcum, Nardostachys jatamamsi, Hypericum perforatum, Corydalis cava, Salvia miltiorrihiza, Cypripedium pubescens, Cymbopogon flexuosus, Melissa officinalis, Monarda didyma, Citrus aurantii,* and *Piscidia piscipula.*

8. Pharmaceutical according to claim 1, wherein the additional pharmacologically active substance is integrated in a way to be released with a delay of 1 to 10 hours.

9. Pharmaceutical according to claim 1, wherein the first pharmacologically active substance is a combination of a sleeping aid for falling asleep and a sleeping agent for sleeping through, the additional pharmacologically active substance is a stimulating agent or dopant, and the sleeping aid is integrated in a way to be released immediately, the sleeping agent is integrated in a way to be released with delay, and the additional pharmacologically active substance is integrated in a way to be released with delay relative to the sleeping agent.

10. Pharmaceutical according to claim 9, wherein the release of the sleeping agent is delayed by 1 to 6 hours and the additional pharmacologically active substance is released with a delay of 2 to 6 hours relative to the sleeping agent.

11. Pharmaceutical according to claim 1, wherein the stimulant or dopant is selected from a methyl xanthine, an amphetamine, pemoline, methylphenidate, or modafinil, or pharmaceutically acceptable salts thereof.

12. Pharmaceutical according to claim 1, wherein the stimulant or dopant is selected from an antidepressant, or dextroamphetamine, or pharmaceutically acceptable salts thereof.

13. Pharmaceutical according to claim 1, wherein the stimulant or dopant is selected from the group consisting of imipramine, desipramine, clomipramine, protriptyline, fluoxetine, paroxetine, sertraline, citalopram, fluvoxamine, amitriptyline, nortriptyline, mirtazepine, venlafaxine, phenelzine, tranylcypromine, nefazodone, trazodone and buprion, or the pharmaceutically acceptable salts thereof.

14. Pharmaceutical according to claim 1, wherein the stimulant or dopant is selected from caffeine, theophylline, or theobromine, or pharmaceutically acceptable salts thereof.

15. Pharmaceutical according to claim 1, wherein the stimulant or dopant is caffeine or a pharmaceutically acceptable salt thereof.

16. Pharmaceutical according to claim 1, wherein the stimulant or dopant is an active ingredient of an extract of caffeine-containing, theophylline-containing, and/or theobromine-containing plants selected from the group consisting of *Paullinia cupana, Crataegus laevigata, Syzyium aromaticum, Ilex paraguariensis, Piper methysticum, Cola acuminita, Folium cocae, Semen myristicae, Ephedra sinica,* and *Tunera diffusa.*

17. A method of treatment comprising asministering a pharmaceutical according to claim 1 to a mammal requiring such treatment.

* * * * *